(12) United States Patent
Lindberg et al.

(10) Patent No.: US 10,812,000 B2
(45) Date of Patent: Oct. 20, 2020

(54) BRAKING ENERGY RECOVERY SYSTEM FOR AN ELECTRIC MOTOR AND METHOD

(71) Applicant: KONINKLIJKE PHILIPS N.V., Eindhoven (NL)

(72) Inventors: Paul Michael Lindberg, San Diego, CA (US); Norbert Daberko, Carlsbad, CA (US)

(73) Assignee: Koninklijke Philips N.V., Eindhoven (NL)

( * ) Notice: Subject to any disclaimer, the term of this patent is extended or adjusted under 35 U.S.C. 154(b) by 331 days.

(21) Appl. No.: 15/747,799

(22) PCT Filed: Jul. 28, 2016

(86) PCT No.: PCT/EP2016/068062
§ 371 (c)(1),
(2) Date: Jan. 26, 2018

(87) PCT Pub. No.: WO2017/017214
PCT Pub. Date: Feb. 2, 2017

(65) Prior Publication Data
US 2018/0212538 A1 Jul. 26, 2018

Related U.S. Application Data

(60) Provisional application No. 62/197,759, filed on Jul. 28, 2015.

(51) Int. Cl.
*H02P 3/00* (2006.01)
*A61M 16/00* (2006.01)
(Continued)

(52) U.S. Cl.
CPC .......... *H02P 3/00* (2013.01); *A61M 16/0066* (2013.01); *B60L 7/10* (2013.01); *F04D 25/06* (2013.01); *H02M 3/1582* (2013.01)

(58) Field of Classification Search
CPC .... H02P 1/00; H02P 1/028; H02P 1/04; H02P 1/12; H02P 1/16; H02P 1/166; H02P 1/20;
(Continued)

(56) References Cited

U.S. PATENT DOCUMENTS 4,761,600 A * 8/1988 D'Atre ...................... H02P 3/22
318/758
7,176,648 B2 * 2/2007 Choi ................... B29C 45/7666
318/625
(Continued)

FOREIGN PATENT DOCUMENTS

EP 1239581 A2 9/2002
JP 2006230040 A 8/2006
(Continued)

*Primary Examiner* — Antony M Paul
(74) *Attorney, Agent, or Firm* — Daniel H. Brean

(57) ABSTRACT

A braking energy recovery system (50) for an electric motor (62) comprises first regulator (52), energy storage device (54), second regulator (56), sensor (60), and controller (58). The first regulator (52) outputs a DC link voltage to the energy storage device (54). The second regulator (56) couples to the energy storage device and outputs a motor drive signal to the electric motor (62). The sensor (60) senses an operating characteristic of the electric motor. The controller (58) outputs to the first regulator an energy management signal (74) that comprises a time variant signal as a function of (i) motor speed and/or (ii) back EMF determined via the sensed characteristic, whereby the first regulator dynamically regulates the DC link voltage to maintain substantially constant an energy balance that comprises a sum of (a) rotational and/or linear kinetic energy of the electric motor and (b) energy stored in the energy storage device.

15 Claims, 6 Drawing Sheets

(51) Int. Cl.
   *B60L 7/10*      (2006.01)
   *F04D 25/06*    (2006.01)
   *H02M 3/158*   (2006.01)

(58) Field of Classification Search
   CPC .... H02P 1/22; H02P 1/26; H02P 1/265; H02P 1/28; H02P 1/42; H02P 1/46; H02P 1/465; H02P 3/00; H02P 3/04; H02P 3/025; H02P 3/06; H02P 3/065; H02P 3/08; H02P 3/12; H02P 3/16; H02P 3/14; H02P 3/18; H02P 3/22; H02P 3/24; H02P 3/1582; H02P 3/26; H02P 4/00; H02P 5/00; H02P 6/00; H02P 6/002; H02P 6/005; H02P 6/006; H02P 6/04; H02P 6/06; H02P 6/08; H02P 6/14; H02P 6/182; H02P 6/24; H02P 21/00; H02P 23/00; H02P 25/00; H02P 27/00; H02P 27/04; H02P 27/06
   USPC .......... 318/374, 375, 376, 400.01, 700, 701, 318/400.02, 599, 721, 799, 800, 801, 430, 318/432
   See application file for complete search history.

(56) References Cited

U.S. PATENT DOCUMENTS

| | | | |
|---|---|---|---|
| 8,513,911 B2* | 8/2013 | Jones | B63H 21/17 |
| | | | 290/43 |
| 9,290,107 B2* | 3/2016 | Shi | B60L 1/00 |
| 2006/0181239 A1 | 8/2006 | Galli et al. | |
| 2011/0068723 A1 | 3/2011 | Maiocchi | |
| 2011/0144547 A1 | 6/2011 | Kusuura | |
| 2012/0227738 A1 | 9/2012 | Virr et al. | |
| 2014/0077737 A1 | 3/2014 | Zhang et al. | |
| 2015/0108925 A1 | 4/2015 | Kanakasabai et al. | |

FOREIGN PATENT DOCUMENTS

| | | |
|---|---|---|
| JP | 2010057242 A | 3/2010 |
| WO | 2015000025 A1 | 1/2015 |

* cited by examiner

BRAKING ENERGY RECOVERY SYSTEM FOR AN ELECTRIC MOTOR AND METHOD

CROSS-REFERENCE TO PRIOR APPLICATIONS

This application is the U.S. National Phase application under 35 U.S.C. § 371 of International Application No. PCT/EP2016/068062, filed on Jul. 28, 2016, which claims the benefit of U.S. Provisional Patent Application No. 62/197,759, filed on Jul. 28, 2015. These applications are hereby incorporated by reference herein.

The present embodiments relate generally to electric motors and more particularly, to a braking energy recovery system for an electric motor drive control circuit and a method of braking energy recovery.

Conventional electric motor drives, e.g., permanent magnet brushless motor drives, are driven by an input power bus which is supplied at a relatively constant voltage level. As shown in FIG. 1, a conventional electric motor drive control circuit 10 includes a voltage regulator 12, DC link capacitor 14, motor regulator 16, sensor 20 and a permanent magnet electric motor 22. As is known in the art, motor 22 includes a rotor and a stator. In addition, motor 22 comprises any one of a single-phase, bi-phase, 3-phase or other configuration, in which the number of phases corresponds to the motor stator having a same number of windings.

With reference still to FIG. 1, the voltage regulator 12 regulates an input voltage, $V_{MAIN}$, into a regulated fixed output voltage, $V_{LINK}$, referred to herein also as a fixed DC link voltage. The fixed DC link voltage comprises a constant voltage level, $V_{LINK}$, and is stored on DC link capacitor 14. After a start-up sequence, during operation of the electric motor drive control circuit 10, the voltage regulator 12 operates to maintain the fixed DC link voltage level on the DC link capacitor 14.

In response to an independent motor control input (e.g., a cycling load control input) ACCEL/DECEL, motor regulator 16 operates to either accelerate or decelerate the motor 22. To accelerate the motor 22, the control input ACCEL/DECEL provides a control signal via signal line 26 to motor regulator 16. Motor regulator 16 is coupled between the DC link capacitor 14 at the regulator's input and the motor 22 at the regulator's output. Motor regulator 16 outputs a regulated motor current, $I_{MOTOR}$, to motor 22. In particular, the regulated motor current supplies current to internal motor windings (not shown) for causing motor 22 to accelerate or decelerate, depending upon the polarity of the regulated motor current.

The electric motor drive control circuit 10 further includes a sensor 20 configured for sensing a characteristic of motor 22 during motor operation and for providing sensor signals via signal line 28. For example, motor 22 can comprise a brushless motor and motor regulator 16 can comprise a current regulator and commutation switches. In this example, sensor 20 can comprise Hall sensors that provide Hall signals with respect to back EMF and phase current, i.e., for use by a motor controller (not shown). The Hall sensor signals are used by the motor controller (not shown) for controlling a commutation sequence of the commutation switches of motor regulator 16 in energizing the motor windings, as is known in the art. In another embodiment, the motor regulator 16 can comprise commutation switches that are controlled in such a manner as to combine the motor regulator and commutation functions.

During rotation of the motor 22, each of motor's stator windings generates a voltage known as back Electromotive Force or back EMF (also referred to as BEMF). The polarity of this back EMF depends on the direction of rotation, which may differ from the polarity of the main voltage, applied to the stator windings. The immediate difference between applied stator winding voltage and back EMF acts upon the winding impedance to determine the magnitude of the winding current and its time rate of change. One factor that influences the magnitude of back EMF generated is the angular velocity or speed of the motor's rotor. As speed increases, the magnitude of back EMF increases.

With reference still to FIG. 1, switching regulator control is continuous with respect to the voltage regulator 12 and motor regulator 16 during motor operation, i.e., acceleration or deceleration. With deceleration, the motor 22 continues to spin in the same direction, but slows down. When motor 22 decelerates, the motor acts like a generator. To start deceleration, motor regulator 16 regulates the applied stator winding voltage to a value lower than the back EMF. The negative difference across the winding impedance causes a reverse current that flows back from the motor 22 into the link capacitor 14, via the motor regulator 16. In other words, back EMF is boosted by regulator 16 to pump current back upstream, via a negative current. It should be noted that deceleration can also occur when commanded motor torque (and corresponding current) are positive, but not sufficient to overcome the mechanical torque load on the motor shaft. In such a case, power regeneration does not occur, because the current is still positive, that is, into the motor.

As disclosed above, the voltage regulator 12 of the electric motor drive control circuit 10 regulates the input voltage, $V_{MAIN}$, into a regulated fixed DC link voltage, $V_{LINK}$. The DC link voltage $V_{LINK}$ is regulated to be constant, i.e., a substantially constant voltage, stored on DC link capacitor 14. Accordingly, the voltage regulator 12 operates to maintain the DC link voltage constant. However, because the operation of voltage regulator 12 is to maintain the DC link voltage to be constant, and because voltage regulator 12 is designed to conduct power in one direction only, a problem arises in that the voltage regulator 12 is incapable of reducing the DC link voltage should the link voltage surge to a higher level than the regulated constant fixed level. It should be noted that it is typical in most power sources for motor drives that regulator 12, and its associated input power source, is a uni-directional power converter, In other words, regulator 12 can pass electrical power in one direction only. For this reason, and to minimize component size, it is necessary that peak input currents to regulator 12 be minimized, even though the power demands of the motor fluctuate considerably as the motor speed changes. To successfully smooth the input power demands requires an energy storage device, such as a DC link capacitor, capable of storing and releasing energy roughly equivalent to that associated with the difference in the kinetic energy in the motor and load at the different speeds encountered in the motor drive application. This is applicable to systems in which motor speed is required to change rapidly enough that deceleration (i.e., braking) occurs rapidly enough that passive deceleration by the load alone is insufficient, and in which the application requires additional negative torque supplied by the motor drive circuits.

Turning now to FIG. 2, there is shown a graphical view 30 of simulated link voltage regulated to a fixed value, motor speed, and boost output current as a function of time for the electric motor drive control circuit 10 of FIG. 1. DC link voltage $V_{LINK}$ as a function of time is indicated by reference numeral 32, wherein the link voltage amplitude (in units of volts (V)) is illustrated on a vertical scale to the upper right-hand portion of the figure. Motor speed as a function of time is indicated by reference numeral 34, wherein the motor speed amplitude (in units of thousands of revolutions per minute (KRPM)) is illustrated on a vertical scale to the mid-left-hand portion of the figure. The boost output current (i.e., current provided via voltage regulator 12) as a function of time is indicated by reference numeral 36, wherein the current (in units of amps (A)) is illustrated on a vertical scale to the lower right-hand portion of the figure. Lastly, time (in units of seconds (s)) is illustrated on the horizontal axis at the bottom of the figure. The graph illustrates a simulation of motor operation, subsequent to a start-up sequence, between the time frame of just prior to 1.4 s and just after 2.4 s.

As illustrated, the link voltage is regulated to be a fixed voltage, and more particularly, 46 V. Some minor variations or fluctuations naturally occur in the link voltage over time as a result of back EMF during motor deceleration. In other words, at approximately 1.3 s, the motor begins to decelerate from approximately 48 KRPM down to 10 KRPM at approximately 1.52 s. During this deceleration time period, the link voltage (note that the link voltage scale is illustrated on the upper-right hand side of the graph) increases from 46 V to approximately 52 V. The small increase in link voltage (i.e., an increase of approximately less than 10 to 13 percent) is mostly due to the negative current pumped back into the link capacitor during the motor deceleration, further as a function of the capacity of the link capacitor.

After 1.52 s, the motor begins to accelerate from 10 KRPM to 48 KRPM at approximately 1.85 s. During this acceleration time period, the link voltage (note that the link voltage scale is illustrated on the upper-right hand side of the graph) decreases from 52 V down to 46 V. The decrease in link voltage (i.e., a decrease of approximately less than 10 to 13 percent) is due to the previously stored excess current now being pumped into the motor 22 from link capacitor 14 for motor acceleration, while the voltage regulator 12 regulates the link voltage to be a fixed voltage of 46 V. Output current of the voltage regulator 12 is shown to require up to 6.5 A being drawn during regulation of the link voltage and acceleration of the motor.

As discussed above with respect to the electric motor drive control circuit 10 of FIG. 1, during motor deceleration, the motor regulator 16 operates to sink current out of the motor 22 and pump the current in to the link capacitor 14, thereby returning energy to the link capacitor. Given that the link capacitor voltage is already regulated to be constant via voltage regulator 12, the capacitor 14 must have enough capacity to store excess charge; otherwise, the voltage of the link capacitor will surge sufficiently higher than the regulated voltage set point to exceed the capacitor maximum voltage rating. As a result, the link capacitor 14 is required to have sufficient excess capacity to absorb and store additional current generated via the motor during deceleration. The requirement for excess capacity is a disadvantage since the physical size of the capacitor must be made larger. This is a further disadvantage in device applications having critical physical size constraints, where circuit board or device real estate is at a premium.

As will be understood from the disclosure contained further herein, the link capacitance of the electric motor drive control circuit 10 of FIG. 1 is on the order of five times (5×) larger than the link capacitance in the electric motor drive control circuit of the braking energy recovery system of FIG. 3, according to the embodiments of the present disclosure. Furthermore, the storage capacitor of the circuit 10 of FIG. 1 is physically more than two times (2×) larger (i.e., more than 100 percent (100%) larger) than the storage capacitor of the circuit of FIG. 3, according to the embodiments of the present disclosure.

Accordingly, an improved method and apparatus for overcoming the problems in the art is desired.

The embodiments of the present disclosure advantageously improve efficiency and drive capability of a motor current regulator in an electric motor drive controller by implementing an intelligent scheme for regulating the voltage supply to the regulator. In addition, the embodiments of the present disclosure are particularly useful where efficient operation is required, especially in battery powered equipment. In particular, the embodiments are useful in battery powered equipment that must employ physically compact energy recovery means for long battery life. Furthermore, while the embodiments are particularly applicable for battery operated devices, the embodiments are also applicable for any power source operated device or system implementation.

According to one embodiment, a braking energy recovery system for an electric motor comprises a first regulator, an energy storage device, a second regulator, a sensing means, and a controller. The first regulator includes an input for receiving an input voltage and an output for outputting a DC link voltage. The first regulator can comprise, for example, a switchmode regulator with an inner control loop implemented as at least one of a current mode and a voltage mode switchmode regulator to affect regulation of the DC link voltage. The energy storage device couples to the output of the first regulator. The second regulator includes an input coupled to the energy storage device and an output for outputting a motor drive signal to the electric motor. The sensing means senses a characteristic of the electric motor operating in response to the motor drive signal. The controller is configured for receiving the sensed characteristic and outputting an energy management signal to the first regulator in response to the sensed characteristic. The energy management signal comprises a time variant signal as a function of at least one of (i) motor speed and (ii) back EMF determined via the sensed characteristic. In addition, the first regulator is responsive to the energy management signal for dynamically regulating the DC link voltage to maintain substantially constant an energy balance that comprises a sum of (a) at least one of rotational and linear kinetic energy of the electric motor and (b) energy stored in the energy storage device.

According to another aspect, with respect to the system, substantially constant comprises a variation of less than a magnitude of change, due to varying speed, in total energy contained in the at least one of the rotational and linear kinetic energy of the electric motor. In other embodiments, a measure of substantially constant is determined according to the requirements of a given electric motor implementation or application.

In yet another aspect, the motor speed includes at least a first speed and a second speed, slower than the first speed, wherein (i) responsive to an energy management signal determined for the first speed, the DC link voltage comprises a first voltage level and (ii) responsive to an energy management signal determined for the second speed, the DC link voltage comprises a second voltage level, higher than the first voltage level.

According to a further aspect, the energy management signal comprises one selected from the group consisting of (i) a voltage regulator setpoint determined according to a look-up table of electric motor speed and DC link voltage values, (ii) a voltage regulator setpoint dynamically determined according to an energy management transfer function of electric motor speed to DC link voltage value, and (iii) an algorithm that operates to minimize a total energy storage capacity required of the energy storage device for a predetermined range of motor speeds.

In another embodiment, the first regulator comprises at least one of a step-up and a step-down converter, and wherein the energy management signal comprises a regulation setpoint signal as a function of motor speed or back EMF. In a further embodiment, the first regulator further comprises a voltage regulator that includes a boost converter and a buck switch coupled to the boost converter, wherein the controller further outputs a boost power enable signal to the voltage regulator, and wherein responsive to the boost power enable signal, the buck switch enables input voltage to the boost converter.

According to another embodiment, the second regulator comprises a motor regulator that includes a current regulator and commutation switches, and wherein responsive to motor regulator control signals received by the motor regulator, (i) the current regulator supplies current to the commutation switches and (ii) the commutation switches output phase dependent motor drive signals to the electric motor. The phase dependent motor drive signals can comprise one of trapezoidal motor drive signals and sinusoidal motor drive signals.

In yet another embodiment, the sensing means comprise at least one selected from the group consisting of Hall sensors, optical encoders, rotary encoders, current sensors, and motor back-EMF sensors.

In another aspect, a slope of a time dependent profile of the DC link voltage and a slope of a time dependent profile of the motor speed or back EMF, synchronized with the time dependent profile of the DC link voltage, substantially match one another with opposite sign, positive or negative, during periods of motor acceleration and periods of motor deceleration.

According to another embodiment, the system includes the electric motor, wherein the electric motor comprises one selected from the group consisting of a brushless electric motor and an electric motor with brushes. According to one aspect, the brushless electric motor further comprises one selected from the group consisting of a single-phase motor, bi-phase motor, a 3-phase motor, and a 12-phase motor. According to another aspect, the electric motor forms part of a blower unit for a medical ventilator that includes an impeller operable for generating an air flow, and wherein the at least one of rotational and linear kinetic energy of the electric motor further comprises at least one of rotational and linear kinetic energy of one or more of the electric motor, the impeller, and any other coupled rotational or linear motion parts. In a further aspect, the electric motor forms part of a drive train for a motor vehicle that includes a power train and wheels, and wherein the at least one of rotational and linear kinetic energy of the electric motor further comprises at least one of rotational and linear kinetic energy of one or more of the electric motor, the power train, the wheels, and any other coupled rotational or linear motion parts.

According to another embodiment, a medical ventilator incorporating a braking energy recovery system for an electric motor, comprises: a blower unit that includes the electric motor and an impeller operable for generating an air flow; a first regulator having an input for receiving an input voltage and an output for outputting a DC link voltage; an energy storage device coupled to the output of the first regulator; a second regulator having an input coupled to the energy storage device and an output for outputting a motor drive signal to the electric motor; means for sensing a characteristic of the electric motor operating in response to the motor drive signal; and a controller for receiving the sensed characteristic and outputting an energy management signal to the first regulator in response to the sensed characteristic. The energy management signal comprises a time variant signal as a function of at least one of (i) motor speed and (ii) back EMF determined via the sensed characteristic. The first regulator is responsive to the energy management signal for dynamically regulating the DC link voltage to maintain substantially constant an energy balance that comprises a sum of (a) at least one of rotational and linear kinetic energy of the electric motor and (b) energy stored in the energy storage device.

According to one aspect, the medical ventilator further includes the first regulator comprising at least one of a step-up and a step-down converter, and wherein the energy management signal comprises a regulation setpoint signal as a function of motor speed or back EMF. In another aspect, the medical ventilator further includes the first regulator further comprising a voltage regulator that includes a boost converter and a buck switch coupled to the boost converter, wherein the controller further outputs a boost power enable signal to the voltage regulator, and wherein responsive to the boost power enable signal, the buck switch enables input voltage to the boost converter.

According to yet another embodiment, a method for energy recovery with a cycling load, comprises: providing a converter having an input for receiving a power from a power source and an output for outputting a regulated power output; providing an energy storage reservoir coupled to the output of the converter; providing a load regulator having an input coupled to the energy storage reservoir and an output for (i) outputting drive energy to the cycling load in response to at least a positive cycle command to the load regulator, and (ii) receiving return energy from the cycling load in response to at least a negative cycle command to the load regulator; sensing, via a load energy sensor, a characteristic of the cycling load operating in response to the drive energy; and receiving, via a controller, the sensed characteristic and outputting, via the controller, an energy management signal to the converter in response to the sensed characteristic, wherein the energy management signal comprises a time variant signal as a function of at least one time variant parameter of the cycling load determined via the sensed characteristic, and wherein the converter is responsive to the energy management signal for dynamically regulating the power output to maintain substantially constant an energy balance that comprises a sum of (a) at least kinetic energy of the cycling load and (b) energy stored in the energy storage reservoir.

In one aspect, the method further includes wherein the energy recovery with a cycling load comprises braking energy recovery with an electric motor. The step of providing the converter further comprises providing a first regulator having an input for receiving an input voltage and an output for outputting a DC link voltage. The step of providing the energy storage reservoir further comprises providing an energy storage device coupled to the output of the first regulator. The step of providing the load regulator further comprises providing a second regulator having an input coupled to the energy storage device and an output for outputting a motor drive signal to the electric motor. The step of sensing further comprises sensing a characteristic of the electric motor operating in response to the motor drive signal. Lastly, the step of receiving further comprises receiving, via the controller, the sensed characteristic and outputting, via the controller, an energy management signal to the first regulator in response to the sensed characteristic, wherein the energy management signal comprises a time variant signal as a function of at least one of (i) motor speed and (ii) back EMF determined via the sensed characteristic, and wherein the first regulator is responsive to the energy management signal for dynamically regulating the DC link voltage to maintain substantially constant an energy balance that comprises a sum of (a) at least one of rotational and linear kinetic energy of the electric motor and (b) energy stored in the energy storage device.

According to a further embodiment, the method further includes wherein the electric motor forms part of one selected from the group consisting of (i) a medical ventilator that includes an impeller operable for generating an air flow, and wherein the at least one of rotational and linear kinetic energy of the electric motor further comprises at least one of rotational and linear kinetic energy of one or more of the electric motor, the impeller, and any other coupled rotational or linear motion parts, and (ii) a motor vehicle that includes a power train and wheels, and wherein the at least one of rotational and linear kinetic energy of the electric motor further comprises at least one of rotational and linear kinetic energy of one or more of the electric motor, the power train, the wheels, and any other coupled rotational or linear motion parts.

Still further advantages and benefits will become apparent to those of ordinary skill in the art upon reading and understanding the following detailed description.

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

Figure 6:
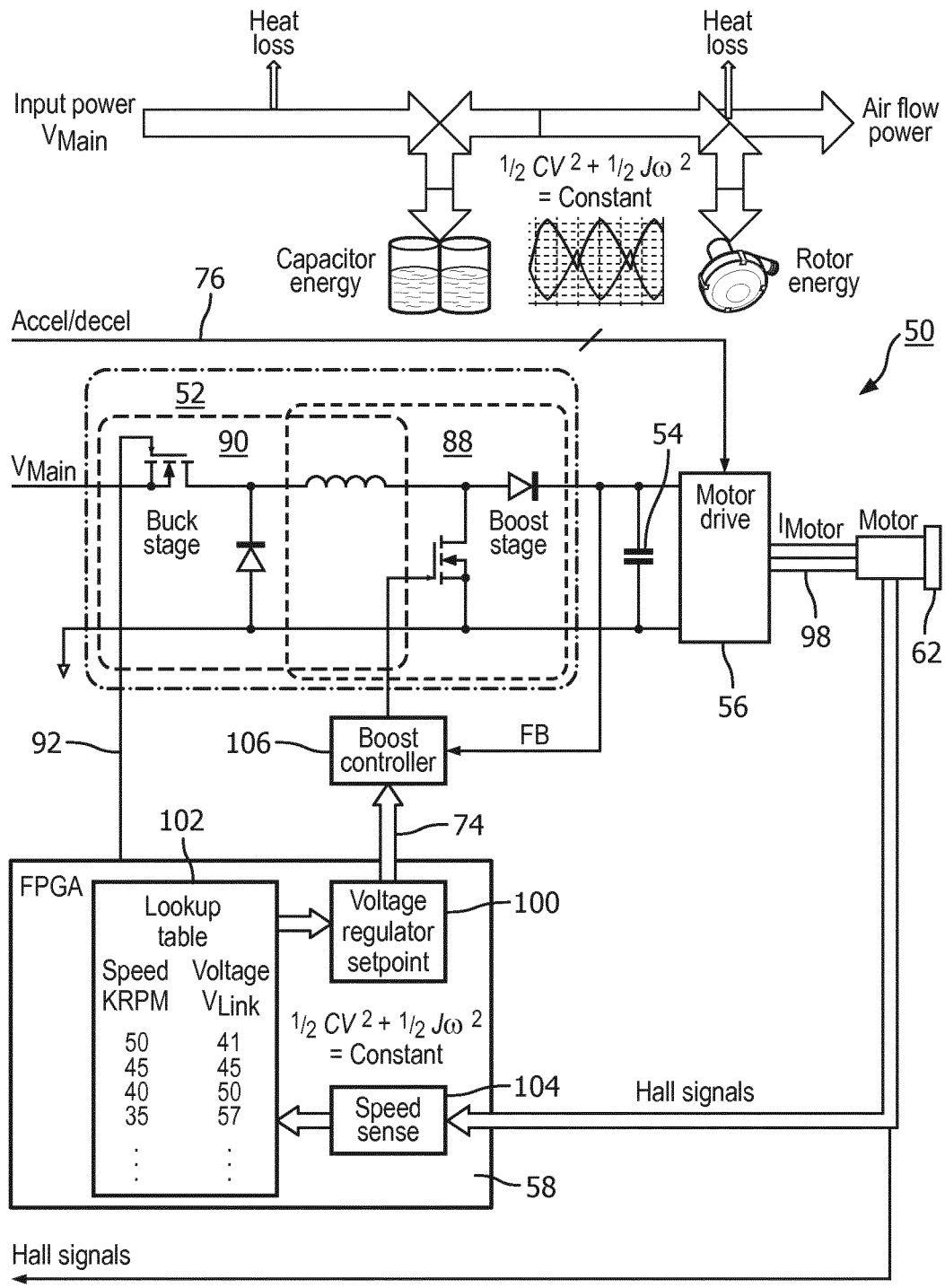
Figure 7:
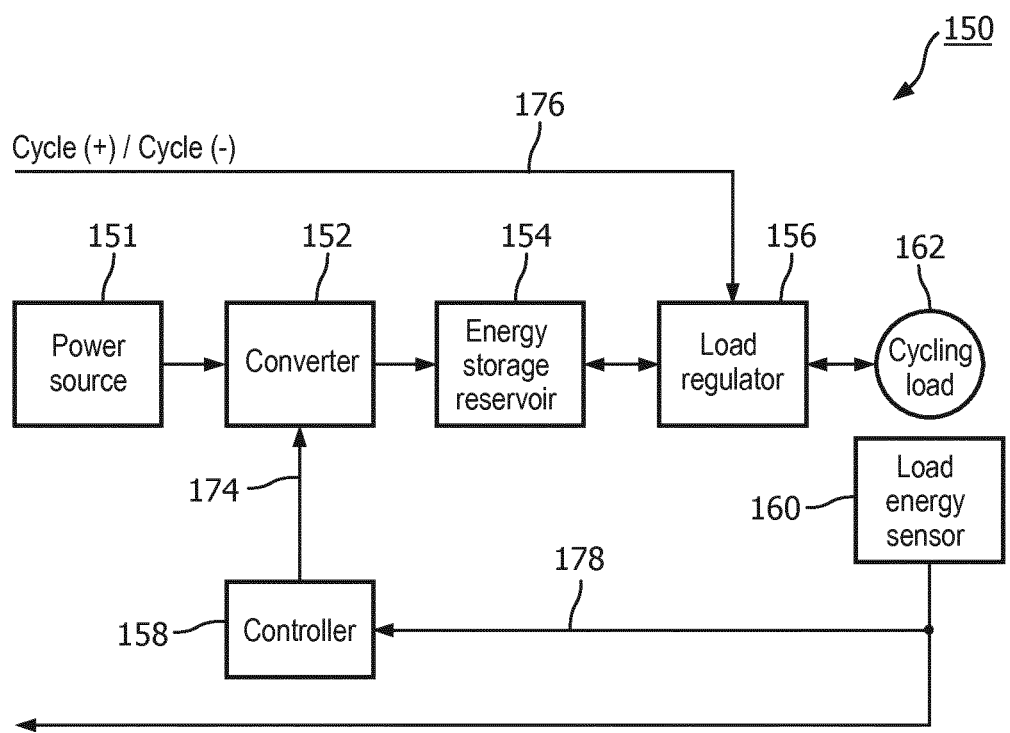

FIG. 6 is a block diagram view of a braking energy recovery system for an electric motor drive control circuit, further including an illustration of energy transfer and recovery, according to yet another embodiment of the present disclosure; and FIG. 7 is a block diagram view of an energy recovery system for a cycling load control circuit according to yet another embodiment of the present disclosure.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

As will be discussed herein, a braking energy recovery system for an electric motor comprises a first regulator, an energy storage device, a second regulator, a sensor for sensing a characteristic of the electric motor, and a controller. The first regulator includes an input for receiving an input voltage $V_{MAIN}$ and an output for outputting a DC link voltage $V_{LINK}(rpm)$. The energy storage device couples to the output of the first regulator. The second regulator includes an input coupled to the energy storage device and an output for outputting a motor drive signal to the electric motor. The sensor is configured for sensing a characteristic of the electric motor operating in response to the motor drive signal. Responsive to receiving and processing the sensed characteristic, the controller outputs an energy management signal EMS(rpm) to the first regulator in response to the sensed characteristic, wherein the energy management signal EMS(rpm) comprises a time variant signal as a function of at least one of (i) motor speed and (ii) back EMF determined via the sensed characteristic. Responsive to the energy management signal, the first regulator is configured for dynamically regulating the DC link voltage $V_{LINK}(rpm)$ to maintain substantially constant an energy balance that comprises a sum of (a) at least one of rotational and linear kinetic energy of the electric motor and (b) energy stored in the energy storage device.

The embodiments of the braking energy recovery system and method discussed herein advantageously provide for a very compact means of storing regenerative motor braking energy. The embodiments further provide a means to deliver a power surge beyond a capability of the main power supply for improved performance.

As can be understood from the disclosure herein, there are disclosed numerous embodiments which include a local and variable voltage DC electrical energy source with storage. A voltage regulator is disclosed which accepts electrical energy from the source to provide a regulated voltage output with variable set point commanded by a time variant voltage output reference Vr(t) and an energy storage capacitor accepting the regulated voltage output.

The embodiments also include a brushless motor drive regulator circuit which pumps energy bi-directional to either accelerate or decelerate the motor; and a motor that accepts as drive power, an output current from the motor drive regulator circuit, and having a rotor of known angular momentum J and a time variant speed profile ω(t). The embodiments further include a voltage regulator which accepts as input the sensed speed profile ω(t) and outputs a voltage output reference Vr(t) with a level determined by an energy efficiency algorithm. The energy efficiency algorithm executes a transfer function to control the voltage reference Vr(t) in such a manner as to maintain a constant total system energy as represented by the sum of (i) the energy in the DC Link storage capacitor and (ii) the energy contained in the angular momentum of the rotor. The algorithm coefficients also include being adjusted so as to minimize the total energy storage capacity required of the DC Link storage capacitor for the range of expected motor speeds ω(t).

The inventors have recognized at least two insights, which include (i) regulating the DC link voltage as a function of motor rpm; and (ii) actively regulating the DC link voltage as a time variant and dynamic set point Vr(t) to hold constant the energy balance equation:

$$E_T = E_K + E_V = \tfrac{1}{2} J \cdot \omega(t)^2 + \tfrac{1}{2} C \cdot Vr(t)^2,$$

where $E_T$ is the total energy in the system, $E_K$ is the total kinetic energy of the system (e.g., in a medical ventilator system or ventilator, the total kinetic energy comprises at least one of the rotational and linear kinetic energy of the motor plus impeller), $E_V$ is the energy stored in capacitor C, J is the angular moment of inertia of the motor plus impeller, ω(t) is the rotational angular velocity, and Vr(t) is the regulated capacitor voltage.

As will be understood from the disclosures herein, electrical power supplied by a battery, offline switching power supply or other conventional means is regulated by a voltage regulator circuit to supply to an energy storage capacitor a dynamically regulated DC link voltage $V_{LINK}$. In one embodiment, the DC link voltage $V_{LINK}$ is supplied to the input of a two quadrant brushless motor drive circuit capable of returning to the energy storage capacitance much of the kinetic energy of the motor during deceleration. The DC link voltage $V_{LINK}$ is further regulated by a regulator circuit (i.e., first regulator), and in one embodiment, by a digital logic circuit to satisfy an equation which holds substantially constant the sum of the rotor kinetic energy and energy stored in the storage capacitance, calculated by the control circuit (i.e., controller) on the basis of sensed motor RPM or Back EMF (BEMF).

Figure 3:
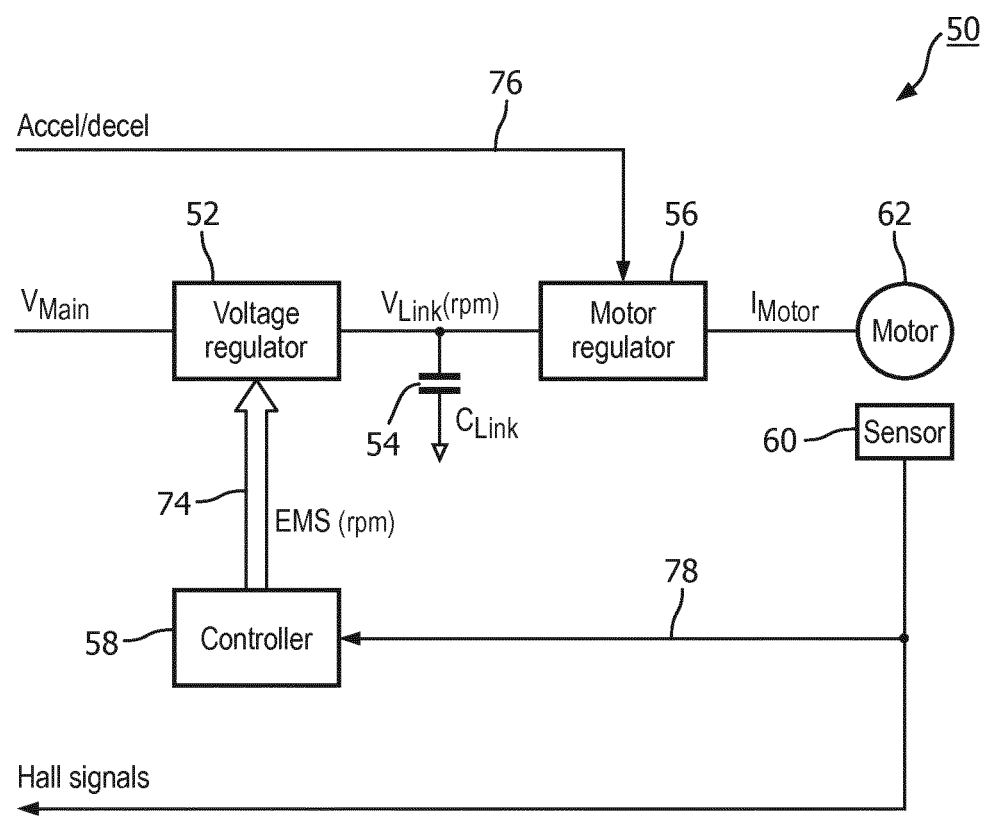
FIG. 3 is a block diagram view of a braking energy recovery system for an electric motor drive control circuit according to an embodiment of the present disclosure.

Referring now to FIG. 3, according to an embodiment of the present disclosure, a braking energy recovery system 50 for an electric motor drive (e.g., permanent magnet motor drives) includes driving the electric motor via an input power bus which is supplied at a voltage level actively regulated as a function of motor rpm. As shown in FIG. 3, the braking energy recovery system 50 for an electric motor drive control circuit includes a voltage regulator 52, DC link capacitor 54, motor regulator 56, controller 58, sensor 60 and a permanent magnet electric motor 62. Motor regulator 56 comprises one or more of (i) a regulation stage combined with a separate commutation stage and (ii) a combined stage which regulates the motor drive with the same switches as are used for commutation. Controller 58 comprises one or more of a microprocessor, microcontroller, field programmable gate array (FPGA), integrated circuit, discrete analog or digital circuit components, hardware, software, firmware, or any combination thereof, for performing various functions as discussed herein, further according to the requirements of a given implementation and/or braking energy recovery application.

In one embodiment, electric motor 62 includes a rotor (not shown) and a stator (not shown). In addition, motor 62 comprises any one of a single-phase, bi-phase, 3-phase, 12-phase or other configuration, in which the number of phases corresponds to the motor stator having a same number of windings. In yet another embodiment, motor 62 can comprise an electric motor with brushes. In a further embodiment, the electric motor forms part of a drive train for an electric vehicle that includes a power train and wheels, and wherein a rotational and/or linear kinetic energy of the electric motor also comprises a rotational and/or linear kinetic energy of one or more of the electric motor, the power train, and the wheels of the electric vehicle. In a yet further embodiment, the electric motor can be of permanent magnet (PM) Synchronous subclasses DC or AC. The DC PM Synchronous motor is characterized primarily by a phase BEMF which changes with a trapezoidal waveshape as the motor rotates, as opposed to an AC PM Synchronous motor that is characterized primarily by a phase BEMF which changes with a sinusoidal waveshape as the motor rotates. In a still further embodiment, the electric motor comprises at least one of a linear motor and a rotary motor, with link voltage controlled as a function of motor speed.

In a yet another embodiment, the commutation circuit (e.g., a portion of the motor regulator) can be one of Synchronous subclasses DC or AC. The DC Synchronous commutation circuit is characterized primarily by an applied phase voltage which changes with a trapezoidal waveshape as the motor rotates, as opposed to an AC Synchronous commutation circuit that is characterized primarily by an average applied phase voltage which changes with a sinusoidal waveshape as the motor rotates.

In a further embodiment, the combination of commutation circuit and brushless motor can be replaced by a brushed permanent magnet DC motor powered by only two input wires, and the commutation circuit electronics being replaced by the arrangement of mechanical commutator contacts and brushes internal to the brushed permanent magnet motor. In this embodiment, the regulated voltage $V_{LINK}$(rpm) corresponds to the voltage applied to the two input wires of the brushed permanent magnet DC motor.

With reference still to FIG. 3, the first regulator 52 can comprise, for example, a switchmode regulator with an inner control loop implemented as at least one of a current mode and a voltage mode switchmode regulator to affect regulation of the DC link voltage. In the embodiment of FIG. 3, the first regulator is shown as a voltage regulator. The voltage regulator 52 regulates an input voltage, $V_{MAIN}$, into a dynamically regulated output voltage, $V_{LINK}$(rpm), as a function of motor speed. The regulated output voltage $V_{LINK}$(rpm) is also referred to herein as a speed controlled DC link voltage. The speed controlled DC link voltage comprises a voltage level that is dynamically varied over a voltage range determined according to the particular requirements of a given braking energy recovery system. For instance, the speed controlled DC link voltage $V_{LINK}$(rpm) is dynamically regulated to vary between a first voltage and a second voltage, higher than the first voltage, for a given dynamic voltage range. In one embodiment, the regulated voltage varies from a first voltage of 45 V to a second voltage of 80 V, having a dynamic range of 35 V. The speed controlled DC link voltage is stored on DC link capacitor 54.

In operation, a start-up sequence is performed to overcome inertia and the rotor of the motor begins rotating. After the start-up sequence, during operation of the braking energy recovery system 50 for an electric motor drive control circuit, the voltage regulator 52 operates to dynamically vary the DC link voltage level on the DC link capacitor 54 in response to energy management signals provided by controller 58 via signal line 74. As will be discussed further herein, the energy management signals (i.e., denoted EMS (rpm) in FIG. 3) are a function of motor speed. In other words, the DC link voltage is made to vary as a function of motor rpm.

In response to an independent control input (e.g., a cycling load control input) ACCEL/DECEL, motor regulator 56 operates to either accelerate, or decelerate, the motor 62. To accelerate the motor 62, the control input ACCEL/DECEL provides a control signal via signal line 76 to motor regulator 56. Motor regulator 56 is coupled between the DC link capacitor 54 at the regulator's input and the motor 62 at the regulator's output. Motor regulator 56 outputs a regulated motor current, $I_{MOTOR}$, to motor 62. In particular, the regulated motor current supplies current to internal motor windings (not shown) for causing motor 62 to accelerate or decelerate, depending upon the polarity of the regulated motor current. In another embodiment, while not shown in the FIG. 3, controller 58 could be configured to provide control signals to motor regulator 56, via signal line 76, in response to the control input ACCEL/DECEL or similar input.

The braking energy recovery system 50 for an electric motor drive control circuit further includes a sensor 60 configured for sensing a characteristic of motor 62 during motor operation and for providing sensor signals to controller 58 via signal line 78. For example, motor 62 can comprise a brushless electric motor and motor regulator 56 can comprise a current regulator and commutation switches. In one embodiment, sensor 60 can comprise Hall sensors that provide signals to controller 58, via signal line 78. While only one sensor 60 and one signal line 78 are illustrated in FIG. 3, other embodiments can include more than one sensor 60 and more than one signal line 78. In one embodiment, the Hall sensor signals are used by a motor controller (not shown) for controlling a commutation sequence of the commutation switches of motor regulator 56 in energizing the motor windings, as is known in the art. In addition, according to an embodiment of the present disclosure, the Hall sensor signals are used by controller 58 for determining motor speed, further for outputting an energy management signal as a function of motor rpm, as discussed further herein. In other embodiments, sensor 60 may also include, for example, one or more of optical encoders, rotary encoders, current sensors, motor back-EMF sensors, or the like, for outputting one or more signals, via signal line 78, to the controller 58, useful for determination of motor speed or back EMF.

During rotation of the motor 62, each of motor's stator windings generates a back EMF voltage. As previously discussed, the polarity of this back EMF depends on the direction of rotation, which may differ from the polarity of the main voltage applied to the stator windings. The immediate difference between applied stator winding voltage and back EMF acts upon the winding impedance to determine the magnitude of the winding current and its time rate of change. One factor that influences the magnitude of back EMF generated is the angular velocity or speed of the motor's rotor. As speed increases, the magnitude of the back EMF increases.

With reference still to FIG. 3, switching regulator control is continuous with respect to the voltage regulator 52 and motor regulator 56 during motor operation, i.e., acceleration or deceleration. With deceleration, the motor 62 continues to spin in the same direction, but slows down. When motor 62 decelerates, the motor acts like a generator. To start deceleration, motor regulator 56 regulates the applied stator winding voltage to a value lower than the back EMF. The negative difference across the winding impedance causes a reverse current that flows back from the motor 62 into the link capacitor 54, via the motor regulator 56. In other words, back EMF is boosted by regulator 56 to pump current back upstream, via a negative current. It should be noted that deceleration can also occur when commanded motor torque (and corresponding current) are positive, but not sufficient to overcome the mechanical torque load on the shaft. In such a case, power regeneration does not occur, because the current is still positive, that is, into the motor.

In addition, with the case of a cycling load addressed by the embodiments of the present disclosure, commanded motor torque also includes a negative commanded motor torque. When commanded motor torque (and corresponding current) is negative, the motor decelerates as the (negative) current is pumped out of the motor and into the link capacitor 14.

As disclosed above, the voltage regulator 52 regulates the input voltage, $V_{MAIN}$, into a dynamically regulated output DC link voltage, $V_{LINK}$(rpm), as a function of motor speed. The speed controlled DC link voltage $V_{LINK}$(rpm) is stored on DC link capacitor 54. The voltage regulator 52 operates to dynamically vary the DC link voltage level on the DC link capacitor 54 in response to energy management signals provided by controller 58 via signal line 74.

As a result, because the operation of voltage regulator 52 dynamically varying the DC link voltage $V_{LINK}$(rpm) as a function of motor speed, the problem discussed herein above, with reference to the voltage regulator 12 of the conventional electric motor drive control circuit 10 as being incapable of reducing the DC link voltage should the link voltage surge to a higher level than the regulated constant fixed level, is advantageously overcome. The fixed constant level output voltage $V_{LINK}$ of voltage regulator 12 of the conventional electric motor drive control circuit 10 disadvantageously operates on the assumption that sufficient stored energy must always be present in the capacitor to accelerate the motor, without consideration of the motor has already accelerated or not. This means that if the motor has already accelerated, the capacitor will upon subsequent deceleration require twice the energy storage capacity to accommodate braking energy that is inherently contained in the motor kinetic energy at its highest anticipated speed.

In contrast, according to the embodiments of the present disclosure, the link voltage level set point is deliberately modified as a function of motor rpm. For example, at high rpm, the motor has already accelerated, and little to no further energy storage is required in the capacitor for purposes of acceleration. Conversely, at low rpm, the motor has already decelerated, and only that amount of energy for subsequent acceleration need be stored. In this way, the braking energy recovery system anticipates and makes room in the DC link capacitor in advance for braking energy of the motor to be returned to the link capacitor. This is advantageously accomplished by controlling, via the dynamically variable output level voltage regulator, the link voltage as a function of motor rpm.

Three parameters considered by the braking energy recovery system according to the embodiments of the present disclosure include link voltage, motor regulator current, and motor voltage (i.e., back EMF). First, the link voltage is deliberately made to function with rpm of the motor. Second, the motor regulator current is controlled as a function of a desired torque for a given motor application. In other words, an independent control input can comprise a desire to increase or decrease the motor speed, and thus current to the motor is ramped up so that the motor will accelerate or down so that the motor will decelerate, respectively. Third, motor voltage dependence on speed is a fixed property of a given motor. When the given motor is operating at a fast speed, the motor back EMF will exhibit a higher voltage. When the motor is operating at a slow speed, the motor back EMF will exhibit a lower voltage.

With respect to the embodiments of the present disclosure, the DC link voltage is being deliberately regulated so that the amplitude of the link voltage is moved in the opposite direction of the motor voltage. In other words, as the motor rpm increases, the DC link voltage is regulated to go down, even though the motor voltage itself is going up. As indicated above, the motor regulator 56 (i.e., the current regulator portion thereof) is controlled via an independent control input as a function of what the motor 62 is to do, i.e., accelerate or decelerate. As motor 62 accelerates, from a slower speed to a faster speed, motor voltage increases from a lower voltage to a higher voltage, and the DC link voltage is regulated to be decreased, via the voltage regulator 52, and vice versa.

In other words, in one embodiment, commanding of motor torque is an independent control input. If the motor 62 is operating at 1 amp and it is desired to increase the current to 2 amps, then the current regulator portion of the motor regulator 56 is controlled with whatever duty cycle its corresponding commutation switches require to have 2 amps going through the motor. In one embodiment, a motor controller (not shown) outputs appropriate duty cycle control signals to motor regulator 56 via signal line(s) 76. Responsive to 2 amps passing through its windings, motor 62 generates more torque, depending on an angular momentum of its rotor and shaft, and will accelerate. As the motor accelerates, the increase in rpm will be detected by the controller 58, via suitable detection circuitry, hardware, software, firmware, or other. As indicated previously, controller 58 comprises one or more of a microprocessor, microcontroller, field programmable gate array (FPGA), integrated circuit, discrete analog or digital circuit components, hardware, software, firmware, or any combination thereof, for performing various functions as discussed herein, further according to the requirements of a given implementation and/or braking energy recovery application.

In accordance with the embodiments of the present disclosure, an increase in motor rpm results in a decrease of the regulation set-point for DC link voltage. At the same time, the motor voltage naturally increases as a function of rpm. As noted herein, a characteristic of the motor is the back EMF, which remains constant for the motor. The motor voltage is proportional to the back EMF multiplied by the motor rpm.

Referring again to FIG. 3, according to the embodiments of the present disclosure, controller 58 receives one or more sensed characteristic, via sensor 60 and signal line(s) 78, and outputs an energy management signal to the voltage regulator 52 in response to the sensed characteristic, i.e., EMS (rpm). The energy management signal comprises a time variant signal as a function of at least one of (i) motor speed and (ii) back EMF determined via the sensed characteristic. The voltage regulator 52 is responsive to the energy management signal EMS(rpm) for dynamically regulating the DC link voltage $V_{LINK}$ (rpm) to maintain substantially constant an energy balance that comprises a sum of (a) at least one of rotational and linear kinetic energy of the electric motor 62 and (b) energy stored in the link capacitor 54 (i.e., an energy storage device). In this manner, the voltage regulator output level set point is modified as a function of motor rpm, i.e., DC link voltage $V_{LINK}$ (rpm).

Figure 4:
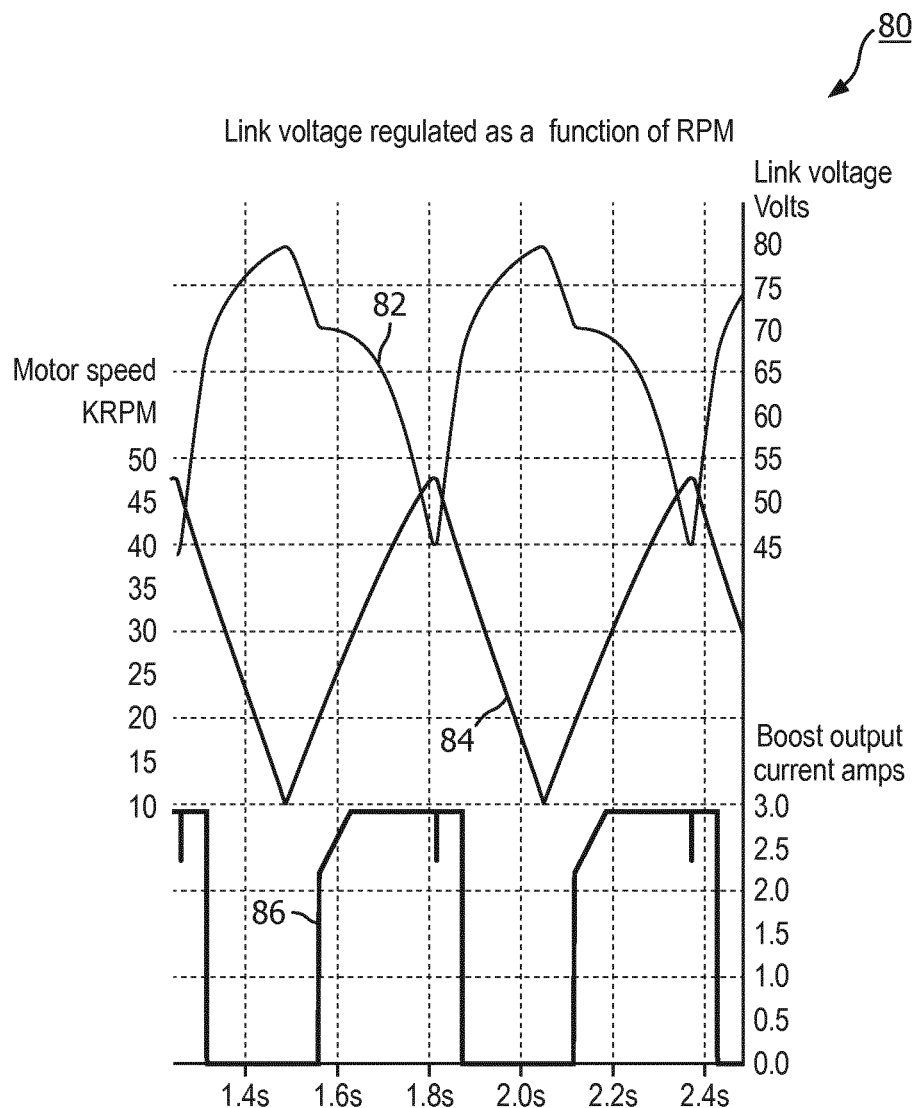
FIG. 4 is a simulated graphical view of link voltage regulated as a function of motor speed or back EMF, motor speed, and boost output current as a function of time of the braking energy recovery system of FIG. 3 according to an embodiment of the present disclosure.

Turning now to FIG. 4, there is shown a graphical view 80 of simulated link voltage dynamically regulated as a function of motor rpm, motor speed, and boost output current as a function of time for the braking energy recovery system 50 for an electric motor drive control circuit of FIG. 3. DC link voltage $V_{LINK}$ (rpm) is illustrated as a function of time and indicated by reference numeral 82, wherein the link voltage amplitude (in units of volts (V)) is illustrated on a vertical scale to the upper right-hand portion of the figure. Motor speed as a function of time is indicated by reference numeral 84, wherein the motor speed amplitude (in units of thousands of revolutions per minute (KRPM)) is illustrated on a vertical scale to the mid-left-hand portion of the figure. The boost output current (i.e., current provided via voltage regulator 52) as a function of time is indicated by reference numeral 86, wherein the current (in units of amps (A)) is illustrated on a vertical scale to the lower right-hand portion of the figure. Lastly, time (in units of seconds (s)) is illustrated on the horizontal axis at the bottom of the figure. The graph illustrates a simulation of motor operation, subsequent to a start-up sequence, between the time frame of just prior to 1.4 s and just after 2.4 s.

As illustrated in FIG. 4, the link voltage 82 is dynamically regulated to vary as a function of motor rpm, and more particularly, to vary between 45 V and 80 V. In other words, at approximately 1.3 s, the motor speed 84 is at 48 KRPM and slows down to 10 KRPM at approximately 1.5 s. During this deceleration time period, the link voltage 82 (note that the link voltage scale is illustrated on the upper-right hand side of the graph) increases from 45 V to approximately 80 V. The significant increase in link voltage 82 (i.e., an increase of approximately 77 or more percent) is due to (i) the negative current pumped back into the link capacitor 54 and (ii) the dynamically regulated link voltage $V_{LINK}$ (rpm) during the motor deceleration, further as a function of the capacity of the link capacitor 54.

After 1.5 s, the motor begins to accelerate from 10 KRPM to 48 KRPM at approximately 1.81 s. During this acceleration time period, the link voltage 82 (note that the link voltage scale is illustrated on the upper-right hand side of the graph) decreases from 80 V down to 45 V. The decrease in link voltage 82 (i.e., a decrease of approximately 77 or more percent) is due to previously stored excess current now being pumped into the motor 62 from link capacitor 54 for motor acceleration, while the voltage regulator 52 dynamically regulates the link voltage 82 to vary as a function of motor rpm, and more particularly, to vary between 80V and 45 V. Output current of the voltage regulator 52 is shown to require up to 2.9 amps being drawn during regulation of the link voltage as a function of motor rpm and acceleration of the motor 62.

With reference still to FIG. 4, it can be observed that a slope of a time dependent profile of the DC link voltage 82 and a slope of a time dependent profile of the motor speed 84 or back EMF, synchronized with the time dependent profile of the DC link voltage, substantially match one another with opposite sign, positive or negative, during periods of motor acceleration (i.e., positive motor speed slope) and periods of motor deceleration (i.e., negative motor speed slope).

As discussed above with respect to the braking energy recovery system 50 for an electric motor drive control circuit of FIG. 3, during motor deceleration, the motor regulator 56 operates to sink current out of the motor 62 and pump the current in to the link capacitor 54, thereby returning energy to the link capacitor. Given that the link capacitor voltage is dynamically regulated as a function of motor rpm via voltage regulator 52, the capacitor 54 needs only to have enough capacity to store excess charge; since, the voltage of the link capacitor will not surge excessively above the dynamically regulated voltage set point as a function of motor rpm. Advantageously, the operation of voltage regulator 52 to dynamically regulate the DC link voltage as a function of motor rpm renders the voltage regulator capable of handling voltage surges. As a result, the link capacitor 54 need only have sufficient excess capacity to absorb and store additional current generated via the motor during deceleration. The providing for only sufficient excess capacity is an advantage since the physical size of the capacitor can be made smaller. This is a further advantage in device applications having critical physical size constraints, where circuit board or device real estate is at a premium.

Figure 1:
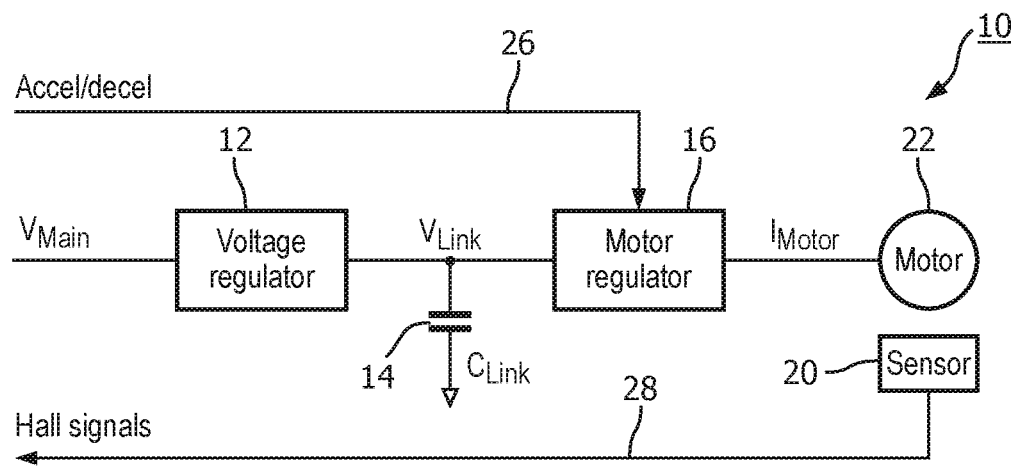
FIG. 1 is a block diagram view of an electric motor drive control circuit known in the art.
Figure 2:
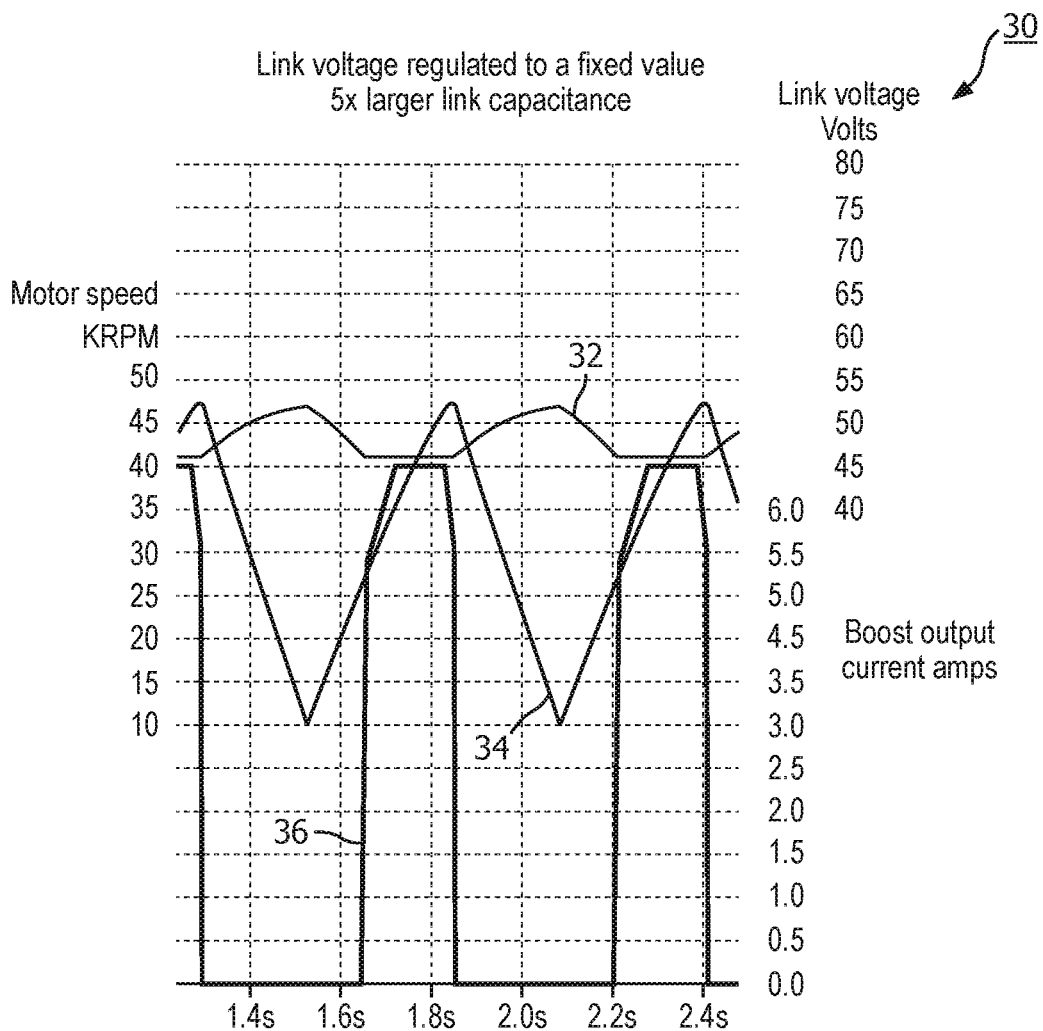
FIG. 2 is a simulated graphical view of link voltage regulated to a fixed value, motor speed, and boost output current as a function of time for the electric motor drive control circuit of FIG. 1.

In comparison, the link capacitance of the electric motor drive control circuit 10 of FIG. 1 is on the order of five times (5×) larger than the link capacitance in the electric motor drive control circuit of the braking energy recovery system of FIG. 3, according to the embodiments of the present disclosure. Furthermore, the storage capacitor 14 of the circuit 10 of FIG. 1 is physically more than two times (2×) larger (i.e., more than 100 percent (100%) larger) than the storage capacitor 54 of the circuit of FIG. 3, according to the embodiments of the present disclosure.

Figure 5:
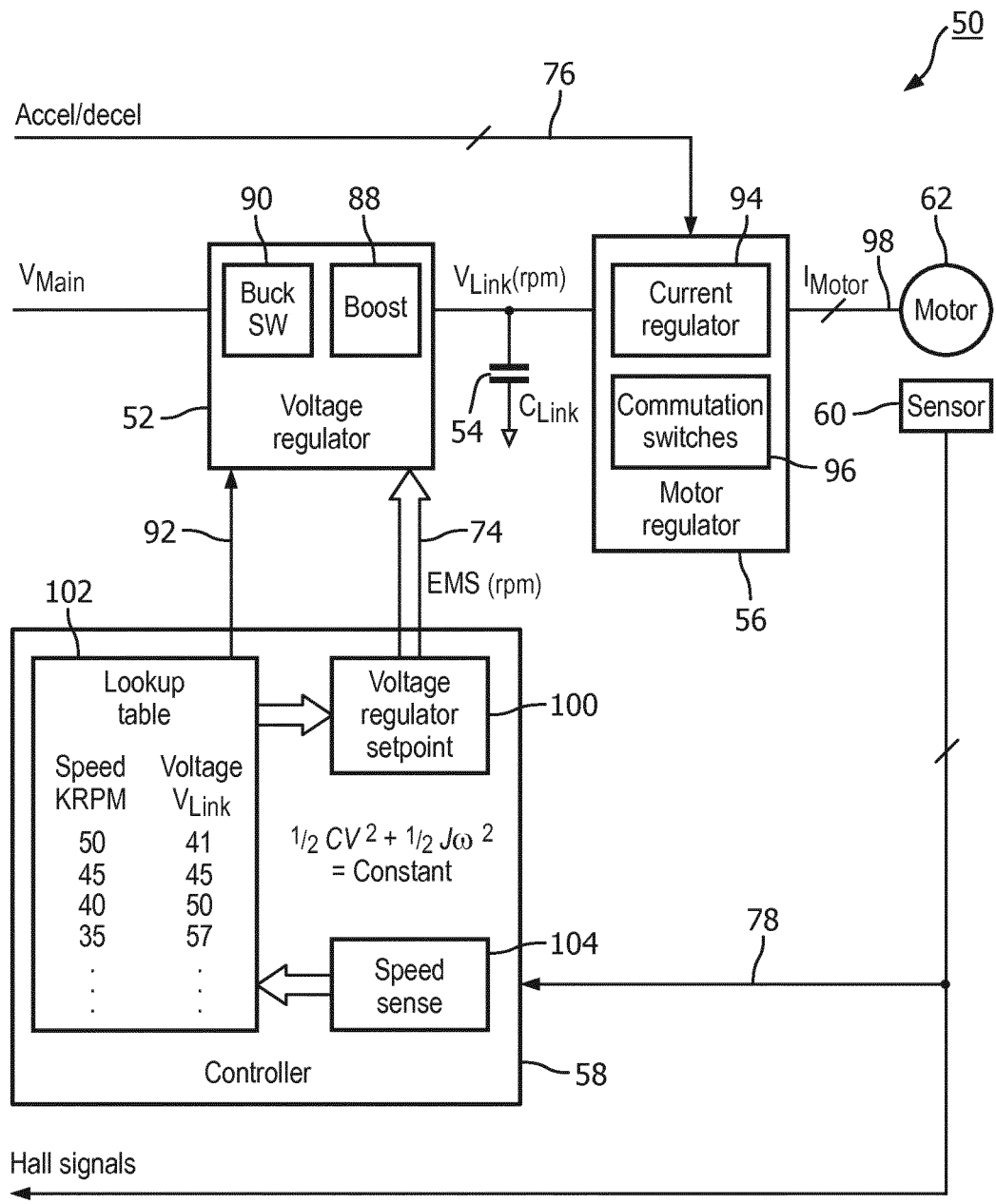
FIG. 5 is a block diagram view of a braking energy recovery system for an electric motor drive control circuit according to another embodiment of the present disclosure.

With reference now to FIG. 5, there is shown a block diagram view of a braking energy recovery system for an electric motor drive control circuit according to another embodiment of the present disclosure. The embodiment of FIG. 5 is similar to that shown and discussed herein with respect to the embodiment of FIG. 3 with the following differences. In the embodiment of FIG. 5, the voltage regulator 52 comprises at least one of a step-up and a step-down converter and the energy management signal 74, EMS(rpm), comprises a boost converter pulse width modulation (PWM) signal as a function of motor speed or back EMF. In a further embodiment, the voltage regulator 52 comprises a boost converter 88 and a buck switch 90 coupled to the boost converter 88. In addition, the controller 58 further outputs a boost power enable signal 92 to the voltage regulator 52, wherein responsive to the boost power enable signal, the buck switch 90 enables input voltage $V_{MAIN}$ to the boost converter 88. It should be noted that while a boost converter and buck switch have been disclosed for the voltage regulator, other topologies are also possible according to the requirements of a given braking energy recovery implementation. For example, there are many potential converter topologies that could be used to make a voltage regulator, such as Single Ended Primary Inductor Converter (SEPIC), Boost, Buck/Boost, Buck, Flyback, Forward, and others.

With reference still to FIG. 5, the motor regulator 56 comprises a current regulator 94 and commutation switches 96. In addition, a motor controller (not shown) outputs motor regulator control signals, via signal lines 76, to the current regulator 94 and commutation switches 96. Responsive to the motor regulator control signals, (i) the current regulator 94 supplies current to the commutation switches 96 and (ii) the commutation switches 96 output phase dependent motor drive signals, via signal lines 98, to the electric motor 62. In a further embodiment, the phase dependent motor drive signals comprise one of trapezoidal motor drive signals and sinusoidal motor drive signals.

With reference to FIGS. 3-5, the motor speed can include at least a first speed and a second speed, slower than the first speed. Responsive to the energy management signal EMS (rpm) determined for the first speed, the voltage regulator 52 regulates the DC link voltage $V_{LINK}$(rpm) to comprise a first voltage level. Responsive to the energy management signal EMS(rpm) determined for the second speed, the voltage regulator 52 regulates the DC link voltage $V_{LINK}$(rpm) to comprise a second voltage level, higher than the first voltage level. In one embodiment, the energy management signal EMS(rpm) comprises a voltage regulator setpoint 100 determined according to a look-up table 102 of electric motor speed and DC link voltage values. In one embodiment, the values for the look-up table comprise interpolated values generated in a spreadsheet modeled to satisfy the expression, $I_C = C \cdot dV/dt$, where $I_C$ is inrush current, C is capacitance, and dV/dt is the controlled rate of rise of the capacitor voltage. In addition, the values can be adjusted for simulated and tested effects of energy loss, and anticipated capacitor value tolerance and variations over time. One example of a look-up table of speed (KRPM) and voltage (VDC) values, according to one embodiment of the present disclosure, is shown in FIGS. 5 and 6. Other sets of speed and voltage values are possible according to the particular requirements of a given braking energy recovery and/or management implementation.

In another embodiment, the energy management signal EMS(rpm) comprises a voltage regulator setpoint 100 dynamically determined according to an energy management transfer function of electric motor speed to DC link voltage value. Motor speed can be determined by controller 58 via a suitable speed sense module 104 in response to a sensed motor characteristic or characteristics via sensor 60. Speed sense module 104 may comprise one or more of hardware, software, firmware, and/or combinations thereof. In a further embodiment, the energy management transfer function can comprise an algorithm with coefficients that operates to minimize a total energy storage capacity required of the link capacitor 54 (i.e., an energy storage device) for a predetermined range of motor speeds.

With reference now to FIG. 6, there is shown a block diagram view of a braking energy recovery system for an electric motor drive control circuit according to yet another embodiment of the present disclosure. The embodiment of FIG. 6 is similar to that shown and discussed herein with respect to the embodiments of FIGS. 3 and 5, with the following differences. In the embodiment of FIG. 6, the motor comprises a 3-phase brushless motor of a blower unit. The blower unit is operable for generating an air flow, for example, of a medical ventilator. The energy management signal EMS(rpm) comprises a voltage regulator setpoint 100 dynamically determined for example via look-up table 102 or according to an energy management transfer function of motor speed to DC link voltage value. Motor speed can be determined by controller 58 via the speed sense module 104 in response to a sensed motor characteristic or characteristics. In this embodiment, Hall sensors (not shown) embodied within the motor 62 provide Hall signals for the sensed characteristics. In addition, the energy management signal EMS(rpm) that comprises a voltage regulator setpoint 100 is provided to a boost controller 106, wherein the boost controller comprises one or more of hardware, software, firmware, and/or combination thereof. The boost controller 106 is configured to switch a MOSFET gate of the boost stage 88 of voltage regulator 52, according to a given duty-cycle in response to the energy management signal EMS(rpm). A feedback loop 108 enables boost controller 106 to ensure a desired dynamically regulated control of the DC link voltage. In addition, controller 58 further outputs the boost power enable signal on signal line 92 to switch a MOSFET gate of the buck stage 90 of voltage regulator 52. Responsive to the boost power enable signal, the MOSFET gate of the buck stage 90 (or buck switch) enables input voltage $V_{MAIN}$ to the boost stage 88 (or boost converter).

Referring now to the top portion of FIG. 6, there is shown a diagrammatic representation of energy management according to the embodiment of the present disclosure. Braking energy is recovered by commanding reverse (i.e., braking) current during rotor deceleration. Recovered energy (i.e., including rotor energy) charges the energy storage capacitor voltage $V_{LINK}$ (i.e., capacitor energy). In the present embodiments, usable stored capacitor energy can be characterized by the expression:

$$Ec = \frac{1}{2} * C(Vpk^2 - Vmin^2),$$

where $E_C$ is usable stored capacitor energy, C is capacitance, $V_{pk}$ is the $V_{LINK}$ peak capacitor voltage, and $V_{min}$ is the $V_{LINK}$ minimum capacitor voltage. From this expression, we recognize that optimal energy storage occurs with relatively large swings in $V_{LINK}$.

Available braking energy storage is optimized by anticipating energy storage for braking and acceleration and by modulating the link capacitor voltage $V_{LINK}$ as a function of RPM to satisfy the following relation:

$$\tfrac{1}{2}CV^2 + \tfrac{1}{2}J\omega^2 = \text{Constant},$$

where C is capacitance, V is capacitor voltage, J is angular moment of inertia of the motor plus impeller (e.g., with respect to a medical ventilator implementation), and ω is the rotational angular velocity. In one embodiment, the braking energy recovery for an electric motor in incorporated into a medical ventilator having a blower motor, and the above expression is a representation for rotor energy balance.

In accordance with yet another embodiment, a method for braking energy recovery with an electric motor comprises providing a first regulator having an input for receiving an input voltage and an output for outputting a DC link voltage; providing an energy storage device coupled to the output of the first regulator; providing a second regulator having an input coupled to the energy storage device and an output for outputting a motor drive signal to the electric motor; sensing, via a sensor, a characteristic of the electric motor operating in response to the motor drive signal; and receiving, via a controller, the sensed characteristic. The method further comprises outputting, via the controller, an energy management signal EMS(rpm) to the first regulator in response to the sensed characteristic. The energy management signal comprises a time variant signal as a function of at least one of (i) motor speed and (ii) back EMF determined via the sensed characteristic. In addition, the first regulator is responsive to the energy management signal for dynamically regulating the DC link voltage to maintain substantially constant an energy balance that comprises a sum of (a) at least one of rotational and linear kinetic energy of the electric motor and (b) energy stored in the energy storage device.

In another embodiment, the method further comprises the electric motor forming part of a drive train for an electric or hybrid motor vehicle that includes a power train and wheels. The at least one of rotational and linear kinetic energy of the electric motor further comprises at least one of rotational and linear kinetic energy of one or more of the electric motor, the power train, the wheels of the motor vehicle, and any other coupled rotational or linear motion parts (e.g., the kinetic energy associated with the linear speed of the moving vehicle mass).

From the disclosures herein, it can be readily understood that the embodiments can be used anywhere an accelerating/decelerating motor drive is used in which compact regenerative braking energy is stored in one or more capacitors. One use for the embodiments of the present disclosure is to drive a blower motor in a medical ventilator in which rhythmic patient breathing requires frequent acceleration and deceleration of the motor. The embodiments of the present disclosure make it possible to shrink the size of energy storage capacitors in the medical ventilator application (which for prior ventilator applications the size of energy storage capacitors have typically been large), and to use less peak power input. The embodiments of the present disclosure may also be useful in motor applications with periodically varying speed profiles, such as a fuel cell electric vehicle employing supercapacitors to enhance peak power demands, and an electrohydraulic artificial heart employing rotary impeller driven hydraulic fluid to compress the pump bladders.

In the case of a motor vehicle that uses an electric motor, such as an electric or hybrid vehicle, the total kinetic energy of the system would include the kinetic energy of the vehicle speed on the road, in addition to at least the rotational and linear kinetic energy of the motor plus power train and wheels. Accordingly, the energy balance equation would read as follows:

$$E_T = E_K + E_V = \tfrac{1}{2}\Sigma(J \cdot \omega(t)^2) + \tfrac{1}{2}M \cdot V(t)^2 + \tfrac{1}{2}C \cdot Vr(t)^2,$$

where M is the mass of the vehicle, V is the vehicle speed on the road, ω and J are each the respective rotational speed and angular moment of inertia of each of the rotating motor and other drive train components, and $\tfrac{1}{2}\Sigma(J \cdot \omega(t)^2)$ is the resulting sum of all rotational kinetic energies in the power train.

With reference now to FIG. 7, there is shown a block diagram view of an energy recovery system 150 for a cycling load (e.g., a cycling load controlled via a cycling load control circuit (not shown)) according to yet another embodiment of the present disclosure. The embodiment of FIG. 7 is similar to that shown and discussed herein with respect to the embodiments of FIGS. 3, 5 and 6, with the following differences. In the embodiment of FIG. 7, the energy recovery system 150 for a cycling load includes controlling the load via an input power source which is supplied at a level actively regulated as a function of a cycling characteristic of the load that stores energy in a cyclic manner. The cycling load control circuit (not shown) is configured to control a load (e.g., mechanical, electrical, hydraulic, or thermal) of cycling characteristic that stores energy in a cyclic manner. This energy can vary with the state of the load, and can be kinetic energy if the load is spinning, or magnetic, if the load is a magnetic coil, or potential if the load is an altitude (e.g., elevators of pressure tanks) or any other form of energy that can be cyclically stored in a load.

As shown in FIG. 7, the energy recovery system 150 for a cycling load control circuit includes a power source 151, converter 152, energy storage reservoir 154, load regulator 156, controller 158, load energy sensor 160 and a load 162 having a cycling characteristic (e.g., a cycling load). The converter 152 regulates the power input from the power source 151 into a dynamically regulated power output as a function of one or more cycling characteristic of the load. The cycling characteristic controlled power output is stored on the energy storage reservoir 154. The converter 152 operates to dynamically vary the energy level on the energy storage reservoir 154 in response to energy management signals provided by controller 158 via signal line(s) 174. Controller 158 of FIG. 7 is similar to controller 58 of FIGS. 3, 5 and 6. In addition, load energy sensor 160 can comprise any suitable sensor or sensors for outputting one or more signals, via signal line 178, to the controller 158, useful for determination of the cycling characteristic of the load 162. In response to an independent control input (e.g., a cycling load control input corresponding to cycle (+) and/or cycle (−)) from a cycling load control circuit (not shown), load regulator 156 operates to either cycle positive (+) or cycle negative (−) the cycling load 162, via signal line 176.

The power source 151 is used to draw power from to power the load 162, drawing that power preferably in as steady a manner as practical. Drawing power in a steady manner is desired so as to minimize the peaks of power relative to the average power drawn from power source 151. In addition, this minimizes the power source component size and stress, regardless of the type of energy used by the load (i.e., electrical, hydraulic, torque, linear motion, etc.).

The problem solved by the embodiment of FIG. 7 is buffering the desirably steady power source by filling an energy storage reservoir via a converter that is controlled in such a way as to hold the total system energy substantially constant. That is, the sum of the cycling load stored energy and the energy reservoir stored energy is held constant. In other words, the energy management satisfies the expression:

System Energy=Load Energy+Reservoir Energy=Substantially Constant.

To accomplish this, the energy recovery system 150 for a cycling load control circuit senses, via the load energy sensor 160 and controller 158, a parameter of the cycling load that provides information about the stored energy in the load. The controller 158 then processes the energy information to control the charging of the energy reservoir in such a way as to minimize the capacity required of the energy reservoir to do its job. In the case of a capacitor, the controller controls the voltage; for a coil, the current; for a spinning rotor energy reservoir, the speed; for a hydraulic tank, the pressure; for a hydroelectric reservoir, the water level. The energy recovery system 150 advantageously minimizes the extreme fluctuations of the level of input power from the power source 151, which additionally can only source power, not sink it. The energy recovery system 150 also advantageously manages the energy storage in the reservoir 154 in such a way as to minimize energy source fluctuations and optimize reservoir capacity.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure can be advantageously used in any motor drive that requires a periodic acceleration and deceleration. In addition, the embodiments of the present disclosure can be advantageously used in any cycling load drive arrangement that controls a load of cycling characteristic that stores energy in a cyclic manner. Furthermore, the embodiments of the present disclosure are also applicable to other devices which convert electrical energy to linear motion, e.g., Linear motors. Linear motors, especially those for industrial applications, almost always move with oscillator motions (exceptions being certain roller coasters and MagLev trains). Electric Linear motors function like 'unrolled' rotary electric motors, and are available in the same subtypes such as induction motor, permanent magnet, AC, DC, brush, brushless, sinusoidal, etc., and the energy storage and drive principles are substantially the same, as discussed herein. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. A braking energy recovery system for an electric motor, comprising:

a first regulator having an input for receiving an input voltage and an output for outputting a DC link voltage;

an energy storage device coupled to the output of the first regulator;

a second regulator having an input coupled to the energy storage device and an output for outputting a motor drive signal to the electric motor; and means for sensing a characteristic of the electric motor operating in response to the motor drive signal; and characterised in that the system further comprises:

a controller for receiving the sensed characteristic and outputting an energy management signal to the first regulator in response to the sensed characteristic, wherein the energy management signal comprises a time variant signal as a function of at least one of (i) motor speed and (ii) back EMF determined via the sensed characteristic, and wherein the first regulator is responsive to the energy management signal for dynamically regulating the DC link voltage to maintain substantially constant an energy balance that comprises a sum of (a) at least one of rotational and linear kinetic energy of the electric motor and (b) energy stored in the energy storage device.

2. The system of claim 1, wherein substantially constant comprises a variation of less than a magnitude of change, due to varying speed, in total energy contained in the at least one of the rotational and linear kinetic energy of the electric motor.

3. The system of claim 1, wherein the motor speed includes at least a first speed and a second speed, slower than the first speed, further wherein (i) responsive to an energy management signal determined for the first speed, the DC link voltage comprises a first voltage level and (ii) responsive to an energy management signal determined for the second speed, the DC link voltage comprises a second voltage level, higher than the first voltage level.

4. The system of claim 1, wherein the energy management signal comprises one selected from the group consisting of (i) a voltage regulator setpoint determined according to a look-up table of electric motor speed and DC link voltage values, (ii) a voltage regulator setpoint dynamically determined according to an energy management transfer function of electric motor speed to DC link voltage value, and (iii) an algorithm that operates to minimize a total energy storage capacity required of the energy storage device for a predetermined range of motor speeds.

5. The system of claim 1, wherein the first regulator comprises at least one of a step-up and a step-down converter, and wherein the energy management signal comprises a regulation setpoint signal as a function of motor speed or back EMF.

6. The system of claim 5, wherein the first regulator further comprises a voltage regulator that includes a boost converter and a buck switch coupled to the boost converter, wherein the controller further outputs a boost power enable signal to the voltage regulator, and wherein responsive to the boost power enable signal, the buck switch (90) enables input voltage to the boost converter.

7. The system of claim 1, wherein the second regulator comprises a motor regulator that includes a current regulator and commutation switches, and wherein responsive to motor regulator control signals received by the motor regulator, (i) the current regulator supplies current to the commutation switches and (ii) the commutation switches output phase dependent motor drive signals to the electric motor.

8. The system of claim 7, wherein the phase dependent motor drive signals comprise one of trapezoidal motor drive signals and sinusoidal motor drive signals.

9. The system of claim 1, wherein a slope of a time dependent profile of the DC link voltage and a slope of a time dependent profile of the motor speed or back EMF, synchronized with the time dependent profile of the DC link voltage, substantially match one another with opposite sign, positive or negative, during periods of motor acceleration and periods of motor deceleration.

10. The system of claim 1, further comprising:
an electric motor, wherein the electric motor comprises one selected from the group consisting of a brushless electric motor and an electric motor with brushes.

11. The system of claim 1, wherein the electric motor forms part of a blower unit for a medical ventilator that includes an impeller operable for generating an air flow, and wherein the at least one of rotational and linear kinetic energy of the electric motor further comprises at least one of rotational and linear kinetic energy of one or more of the electric motor, the impeller, and any other coupled rotational or linear motion parts.

12. The system of claim 1, wherein the electric motor forms part of a drive train for a motor vehicle that includes a power train and wheels, and wherein the at least one of rotational and linear kinetic energy of the electric motor further comprises at least one of rotational and linear kinetic energy of one or more of the electric motor, the power train, the wheels, and any other coupled rotational or linear motion parts.

13. A medical ventilator incorporating a braking energy recovery system for an electric motor, comprising:
a blower unit that includes the electric motor and an impeller operable for generating an air flow; and
a braking energy recovery system (50) as in claim 1.

14. A method for energy recovery with a cycling load, comprising:
providing a converter having an input for receiving a power from a power source and an output for outputting a regulated power output;
providing an energy storage reservoir coupled to the output of the converter;
providing a load regulator having an input coupled to the energy storage reservoir and an output for (i) outputting drive energy to the cycling load in response to at least a positive cycle command to the load regulator, and (ii) receiving return energy from the cycling load in response to at least a negative cycle command to the load regulator; and
sensing, via a load energy sensor, a characteristic of the cycling load operating in response to the drive energy;
characterised in that the method further comprises:
receiving, via a controller, the sensed characteristic and outputting, via the controller, an energy management signal to the converter in response to the sensed characteristic, wherein the energy management signal comprises a time variant signal as a function of at least one time variant parameter of the cycling load determined via the sensed characteristic, and wherein the converter is responsive to the energy management signal for dynamically regulating the power output to maintain substantially constant an energy balance that comprises a sum of (a) at least kinetic energy of the cycling load and (b) energy stored in the energy storage reservoir.

15. The method of claim 14, wherein the energy recovery with a cycling load comprises braking energy recovery with an electric motor, wherein:
providing the converter further comprises providing a first regulator having an input for receiving an input voltage and an output for outputting a DC link voltage;
providing the energy storage reservoir further comprises providing an energy storage device coupled to the output of the first regulator;
providing the load regulator further comprises providing a second regulator having an input coupled to the energy storage device and an output for outputting a motor drive signal to the electric motor;
sensing further comprises sensing a characteristic of the electric motor operating in response to the motor drive signal; and
receiving further comprises receiving, via the controller, the sensed characteristic and outputting, via the controller, an energy management signal to the first regulator in response to the sensed characteristic, wherein the energy management signal comprises a time variant signal as a function of at least one of (i) motor speed and (ii) back EMF determined via the sensed characteristic, and wherein the first regulator is responsive to the energy management signal for dynamically regulating the DC link voltage to maintain substantially constant an energy balance that comprises a sum of (a)

at least one of rotational and linear kinetic energy of the electric motor and (b) energy stored in the energy storage device.

\* \* \* \* \*